US00PP31851P3

(12) United States Plant Patent
Moon

(10) Patent No.: US PP31,851 P3
(45) Date of Patent: Jun. 9, 2020

(54) ***STYRAX* TREE NAMED 'SJMTF'**

(50) Latin Name: *Styrax japonicus*
Varietal Denomination: SJMTF

(71) Applicant: SOUTHERN SELECTIONS, LLC, Loganville, GA (US)

(72) Inventor: Dwayne C. Moon, Logansville, GA (US)

(73) Assignee: Southern Selections, LLC, Logansville, GA (US)

( * ) Notice: Subject to any disclaimer, the term of this patent is extended or adjusted under 35 U.S.C. 154(b) by 0 days.

(21) Appl. No.: 16/350,364

(22) Filed: Nov. 7, 2018

(65) Prior Publication Data

US 2020/0146195 P1 May 7, 2020

(51) Int. Cl.
*A01H 5/00* (2018.01)
*A01H 6/00* (2018.01)
*A01H 5/02* (2018.01)

(52) U.S. Cl.
USPC ..... Plt./216
CPC ..... *A01H 6/00* (2018.05); *A01H 5/02* (2013.01)

(58) Field of Classification Search
USPC ..... Plt./216
CPC ..... A01H 6/00; A01H 5/02
See application file for complete search history.

*Primary Examiner* — Keith O. Robinson
(74) *Attorney, Agent, or Firm* — Stinson LLP

(57) ABSTRACT

A new and distinct variety of Japanese Snowbell tree named 'SJMTF' substantially as herein shown, illustrated and described, characterized particularly as to novelty by its columnar growth habit; dominant central leader, smaller, darker leaves; and its prolific blooms. These genetic traits are unique to my new variety and can be consistently reproduced by asexual propagation.

7 Drawing Sheets

Latin name of genus and species: *Styrax japonicus*.

Varietal denomination: Japanese Snowbell tree which I have named 'SJMTF'.

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to a new and distinct variety of Japanese Snowbell tree (*Styrax japonicus*). The variety is designated by the cultivar name 'SJMTF'.

Discovery

The new *Styrax japonicus* 'SJMTF' variety is the result of a selection made by the inventor, Dwayne Moon, from a tree which was crossed within the species (a male *Styrax japonicus* named MTF101 and a female *Styrax japonicus* named MTF201; not patented) at a farm in Madison, Ga. In 2014, the inventor began to take grafts from the mature parent tree and planted them in production fields in Washington, Ga. where evaluation of this tree continues.

Propagation

'SJMTF' was asexually propagated by the method of grafting at my direction in the summer of 2014 at a farm in Washington, Ga. This propagation from grafting on *Styrax japonicus* understock and resulting progeny has proven the characteristics of my new variety to be genetically stable. Furthermore, these observations have confirmed that 'SJMTF' represents a new and improved variety of Japanese Snowbell tree as particularly evidenced by the columnar growth habit; dominant central leader; smaller, darker leaves; and its prolific white blooms. These genetic traits are unique to 'SJMTF' and can be consistently reproduced by asexual propagation.

Uniqueness

The characteristics of 'SJMTF' distinguish it from other typical seedling Japanese Snowbell trees and the known cultivars. At the time this tree was selected, I observed 'SJMTF' Japanese Snowbell tree as a two inch caliper tree exhibiting a columnar growth habit; dominant central leader, smaller, darker leaves like (RHS 147A) in summer; and prolific white blooms from May to June. These traits make 'SJMTF' significantly different from the species which is rounded to broad-rounded. The traits of 'SJMTF' also make it uniquely different from other cultivars such as 'Evening Shade' (U.S. Plant Pat. No. 24,168P2) which has foliage that emerges dark purple, 'Angyo Dwarf' (patent unknown) which has a dwarf habit; 'Carillon', (patent unknown) 'Pendula', (patent unknown) and 'Fragrant Fountains' (U.S. Plant Pat. No. 19,664) which all have weeping forms; 'Pink Chimes' (patent unknown), and 'Rosea' (patent unknown) which have pink flowers; 'Issai' (patent unknown) which is a faster grower; 'Emerald Meadow' (patent unknown) and 'Snowcone' (patent unknown) which are pyramidal in habit; 'Emerald Pagoda' (patent unknown) which has larger leaves, and larger, heavier flowers; 'Crystal' (patent unknown) which has an upright fastigiate habit with flowers which have purple pedicels; 'Kusan' (patent unknown) which has a compact, globe-shaped form; and 'Snow Charm' (patent unknown) and 'Snowfall' (patent unknown) which both have rounded habits.

Use

'SJMTF' was observed for a period of several years and is believed to be particularly useful as a specimen tree in commercial and residential areas, and is worthy of extensive landscape use from golf courses, commercial sites, and parks. 'SJMTF' will also benefit growers who will profit from the desired look of a high quality flowering tree due to its columnar growth habit, very dark foliage, along with abundant white bell-shaped blooms.

SUMMARY OF THE INVENTION

Background

Seedling Japanese Snowbell is a small, low-branched tree which develops a rounded to broad-rounded crown with a wide-spreading, horizontal branching pattern. Mature native Japanese Snowbell trees are typically 20 to 30 feet in height with a spread of 15 to 25 feet. Japanese Snowbell tree is native to China, Korea, and Japan being introduced in 1862. It is noted for its pendulous clusters of bell-shaped, mildly fragrant, waxy white flowers that bloom in May-June. Flowers give way to greenish-brown, olive-shaped drupes that often persist into late autumn. Elliptic-ovate, glossy, medium to deep green leaves. Fall color is usually insignificant, however leaves may sometimes turn yellow to red. Japanese Snowbell tree variety 'SJMTF' is an improvement over the species in that it is asexually reproduced with a columnar growth habit with a dominant central leader; smaller, darker leaves like (RHS 147A) in summer; and prolific white blooms from May to June. The ultimate height and width of a fully grown, mature 'SJMTF' is not known. The new Japanese Snowbell tree 'SJMTF' variety is expected to perform as well as the species varieties.

BRIEF DESCRIPTION OF THE DRAWINGS

The accompanying photographs depict the overall appearance and color of the tree and foliage of the new Japanese Snowbell tree 'SJMTF' variety in reference to trees at 5 years of age as nearly as is reasonably possible to make the same in a color illustration of this character.

DETAILED DESCRIPTION OF THE INVENTION

Botanical Description of the Plant

Figure 1:
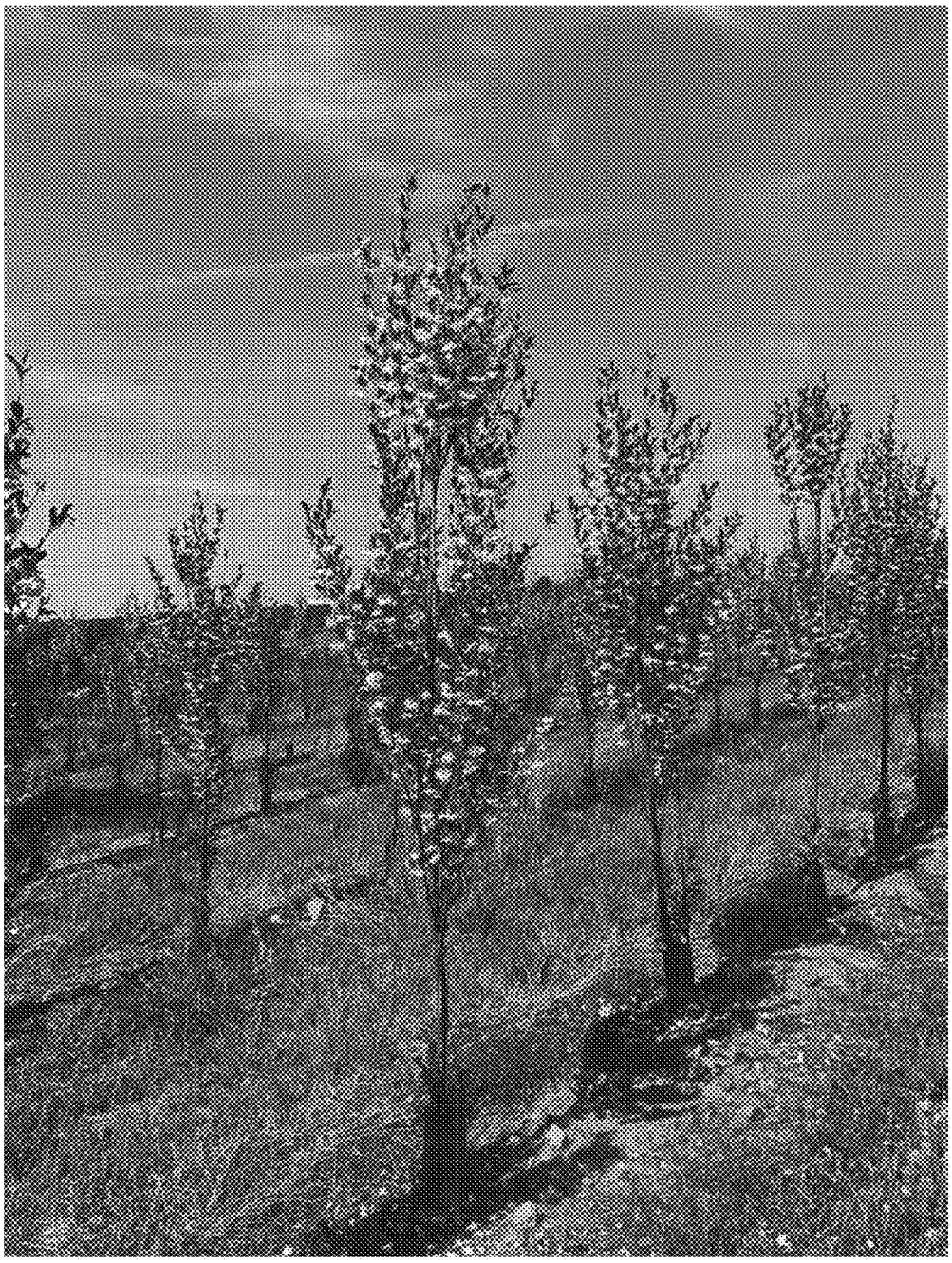
FIG. 1 shows 'SJMTF' taken in the production field in Washington, Ga. in Wilkes County in 2018.
Figure 2:
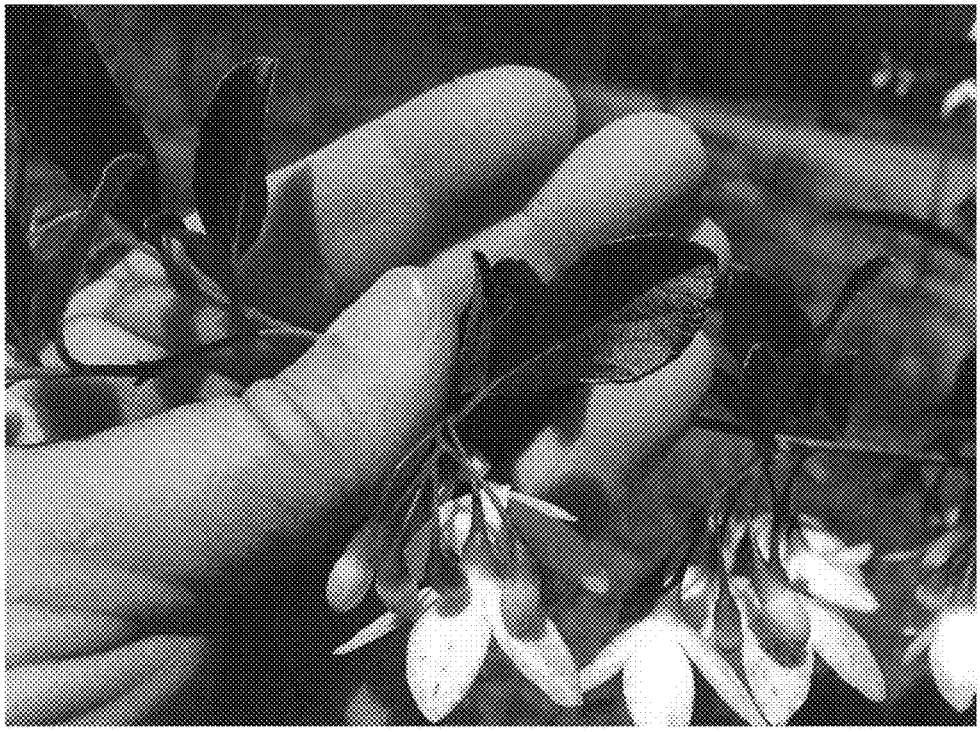
FIG. 2 shows the small, dark leaves of 'SJMTF'.
Figure 3:
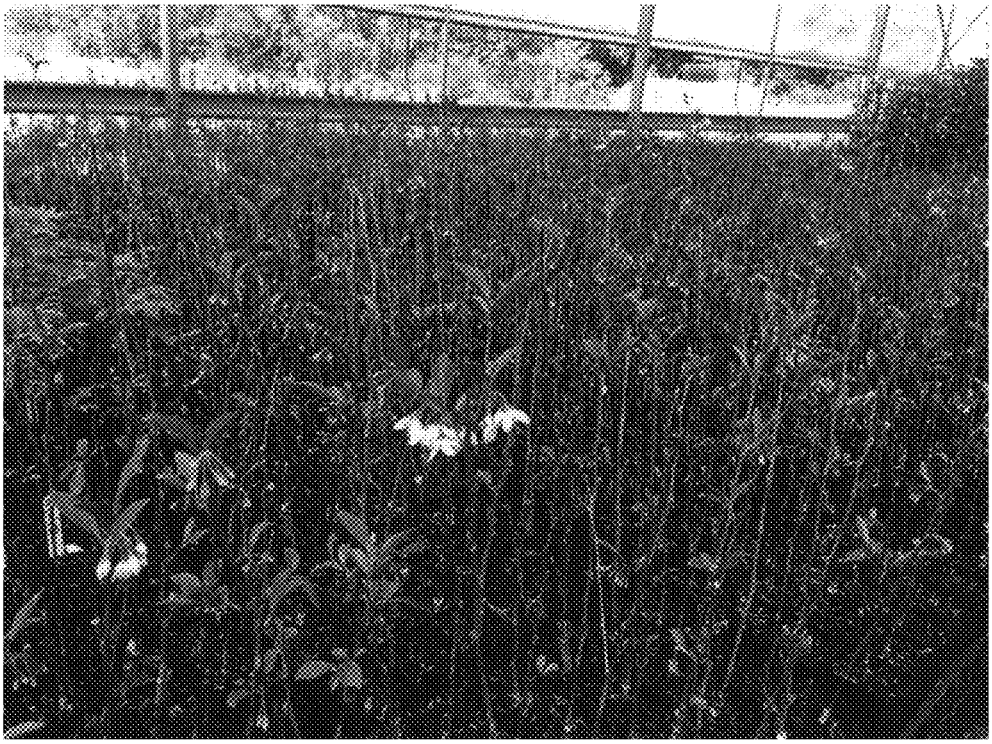
FIG. 3 shows propagation of the rooted cuttings of 'SJMTF'.
Figure 4:
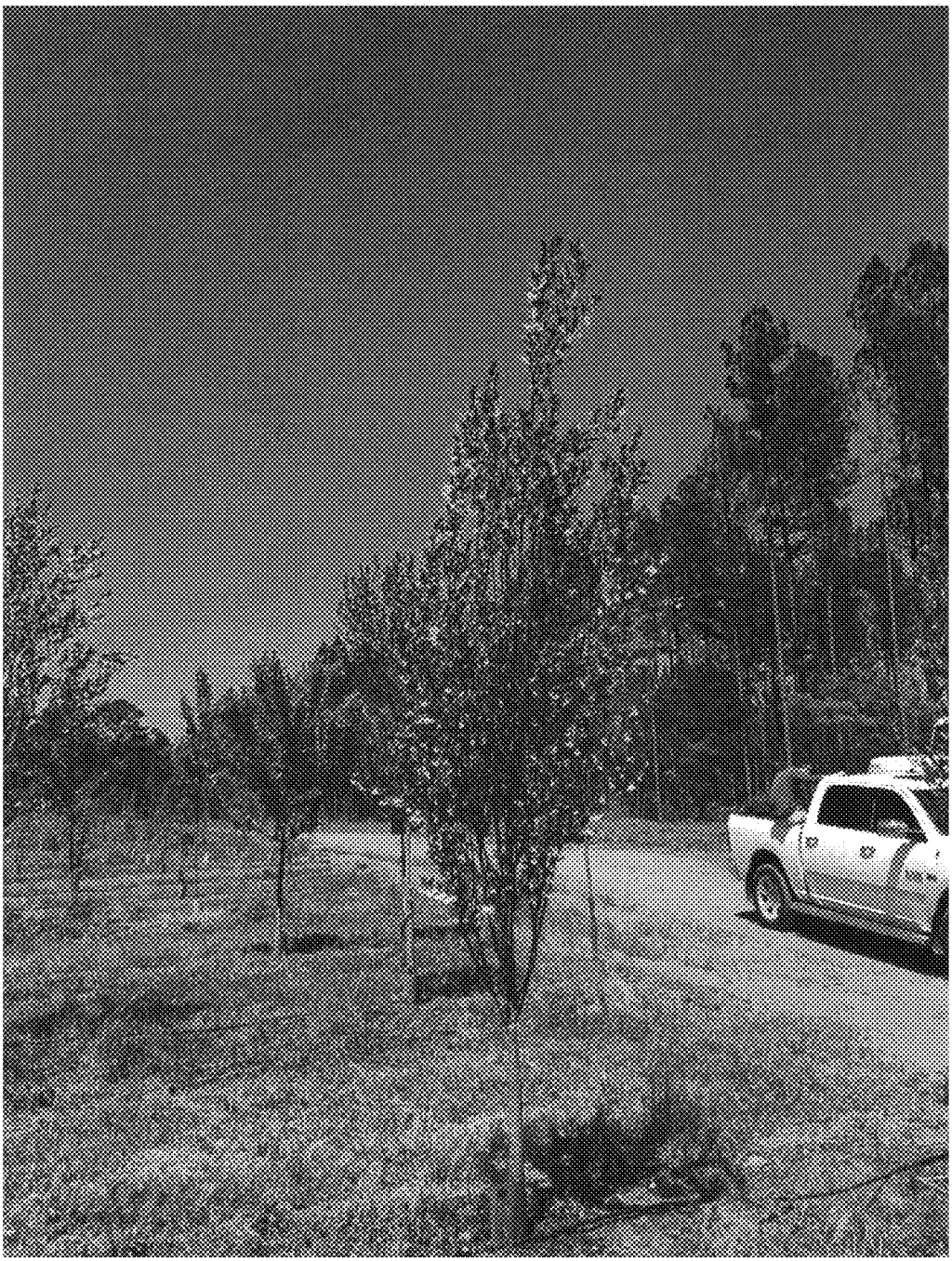
FIG. 4 shows the columnar growth habit of 'SJMTF'.
Figure 5:
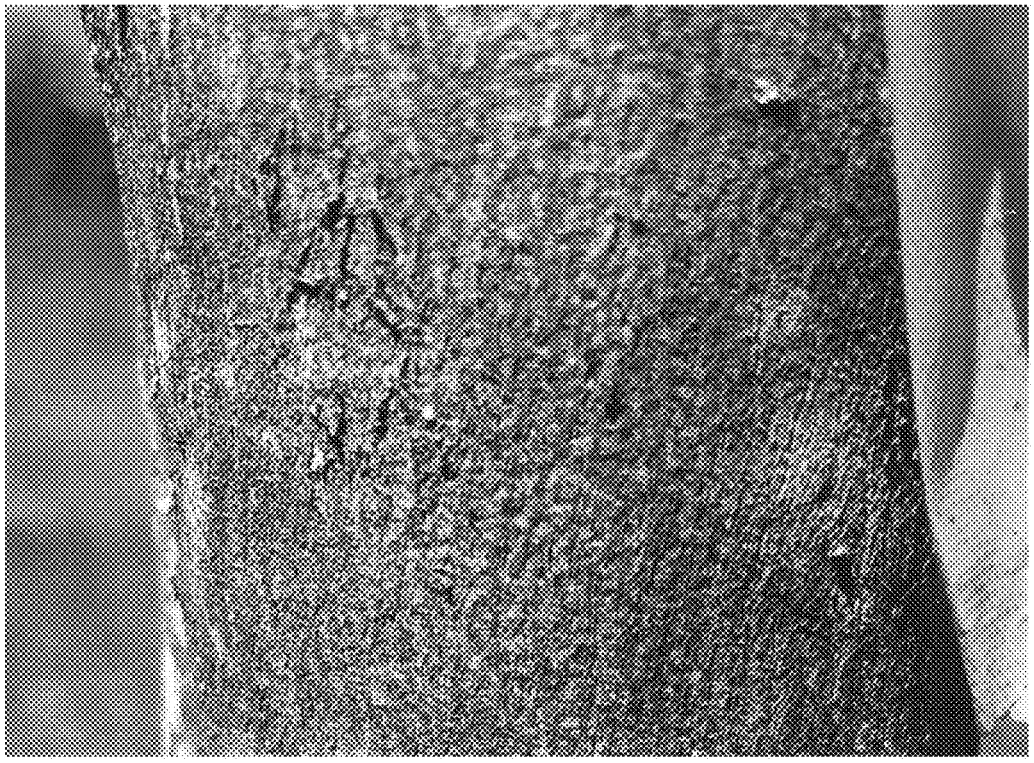
FIG. 5 shows the bark of 'SJMTF'.
Figure 6:
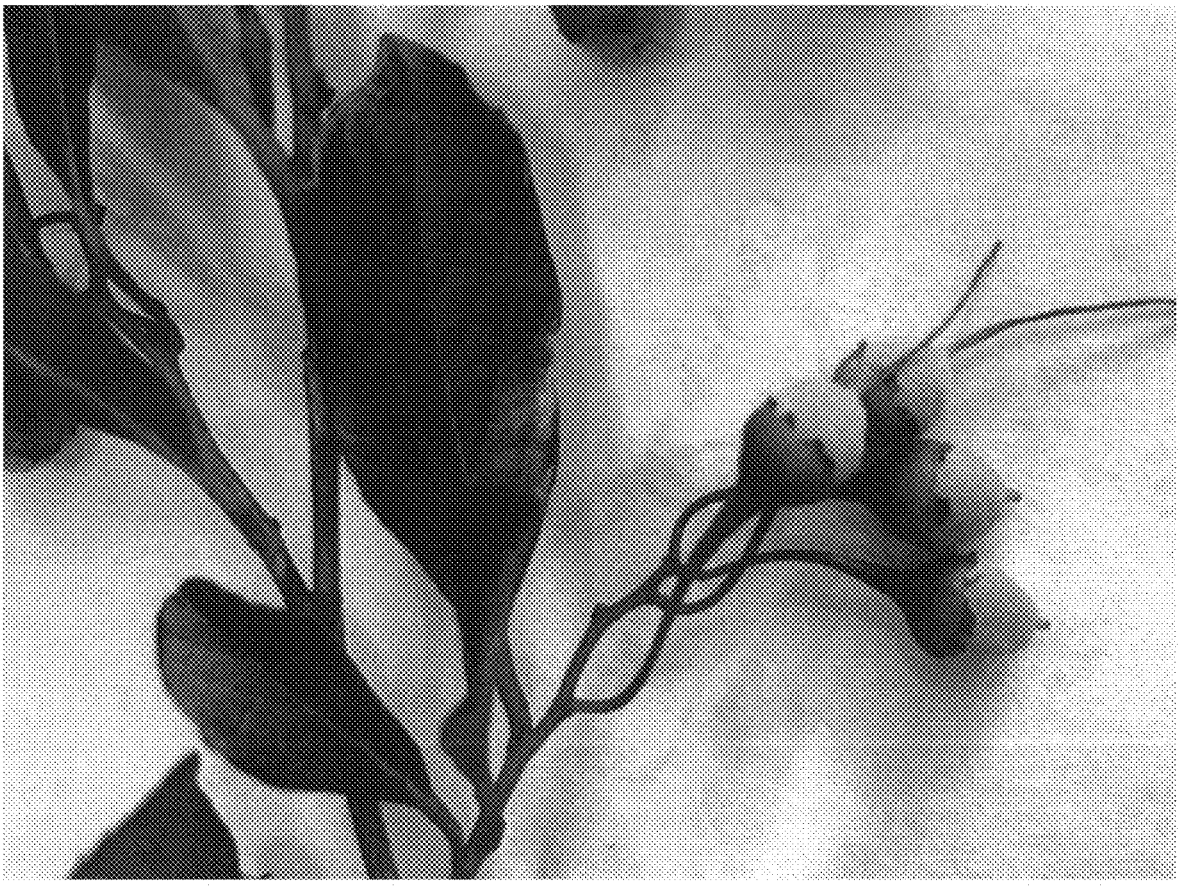
FIG. 6 shows the fruit of 'SJMTF'.
Figure 7:
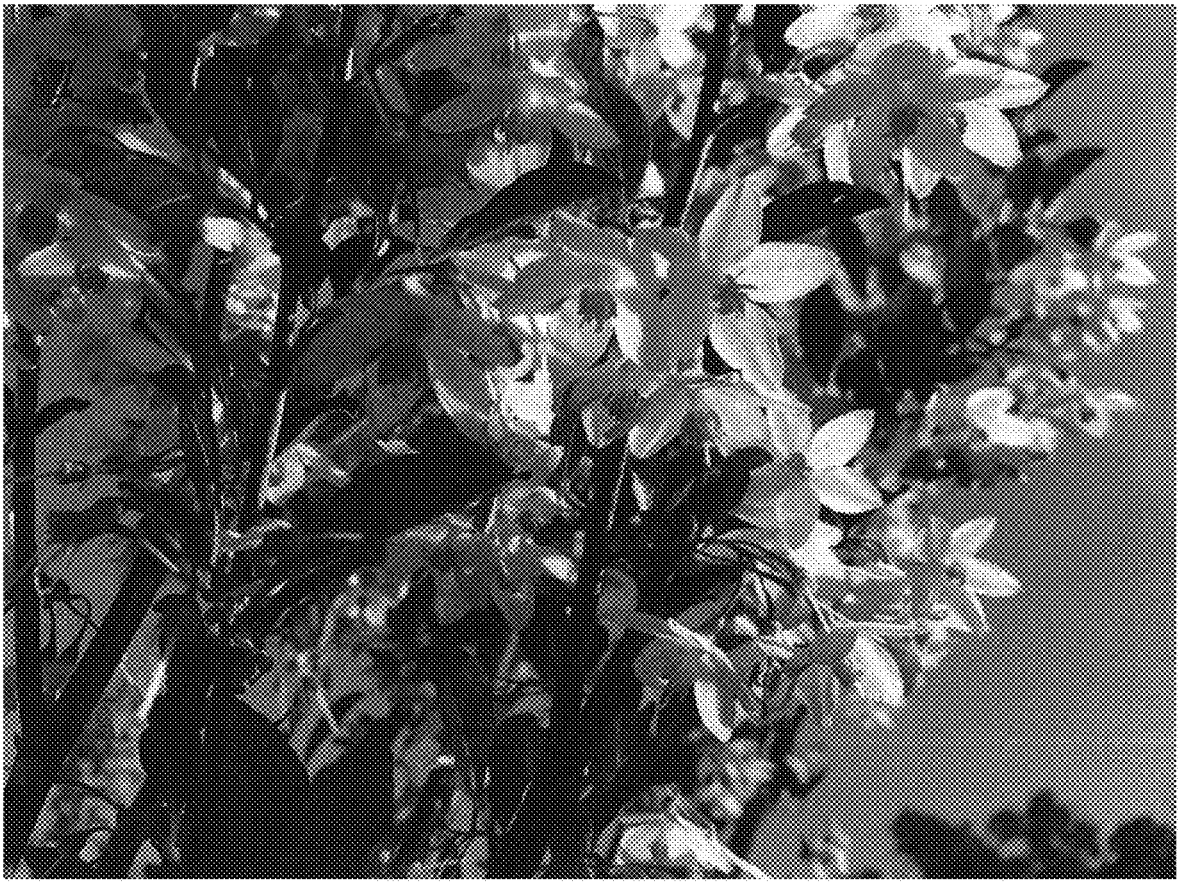
FIG. 7 shows the prolific flowers of 'SJMTF'.

The following is a detailed description of 'SJMTF' Japanese Snowbell tree with color terminology in accordance with The Royal Horticulture Society (R.H.S.) Colour Chart (2001) except where the context indicates a term having its ordinary dictionary meaning.

'SJMTF' has not been observed under all growing conditions, and variations may occur as a result of different growing conditions. All progeny of 'SJMTF', insofar as have been observed by the inventor, have remained genetically stable in all characteristics described hereinafter. Other than as set out hereinafter, as of this time, no other characteristics have been observed by the inventor that are different from common Japanese Snowbell trees.

Scientific name: *Styrax japonicus* 'SJMTF'.

Parentage: Naturally occurring cross-pollinated seedling with the species, Japanese Snowbell tree growing in a cultivated field in Madison, Ga. and now grafted and planted into production fields in Washington, Ga.

Propagation:

- *Root description*.—'SJMTF' is grafted onto seedling rootstocks, so the root system is expected to be typical of the species, which is somewhat coarse.
- *Root color*.—Gray-brown like (RHS N199).

Tree:

- *Growth habit*.—Upright columnar branch structure.
- *In a container or in the ground*.—In ground.
- *Height*.—Approximately 12' foot at 5 years.
- *Plant spread*.—Approximately 4 foot at 5 years.
- *Growth rate*.—Height to width ratio 4-1. Average caliper growth rate between ½ to ¾ inch per year.
- *Trunk diameter*.—Approximately 2 inch caliper measured at 12 inches above the ground at 5 years. Rises through the canopy and maintains a central leader.
- *Trunk*.—Trunk bark texture: Smooth consistency but showing irregular and interlacing fissures. Trunk bark color: Gray-Brown like (RHS N199).

Leaves:

- *Arrangement*.—Alternate.
- *Sheen*.—Smooth; upper surface glossy; lower surface matte.
- *Shape of leaf blade*.—Elliptical.
- *Leaf apex shape*.—Acute.
- *Leaf base shape*.—Cuneate.
- *Leaf margin characteristics*.—Serrate.
- *Description of any leaf pubescence*.—None.
- *Leaf length*.—4 cm to 6 cm.
- *Leaf width*.—1.5 cm to 2.75 cm.
- *Leaf internode length*.—About 1.5 cm.
- *Leaf venation description*.—Pinnate.
- *Petiole length*.—1 cm to 1.5 cm.
- *Petiole diameter*.—2 mm.
- *Petiole color*.—Green like (RHS N138A).
- *Petiole texture*.—Smooth with light pubescence when foliage emerges.
- *Spring leaf color*.—First emerging leaves are green like (RHS 139B).
- *Summer leaf color*.—Upper leaf surface is a very dark green foliage like (RHS 139A) while the lower leaf surface is green like (RHS N138A). The center vein is green like (RHS 138B).
- *Fall color*.—Fall color remains green (RHS 139A) with no real significant change in fall.
- *Pubescence*.—None.

Flowers:

- *Shape*.—Individually, each flower is bell-shaped.
- *Size*.—Individual flowers have an average diameter of 1.25 to 3 cm drupes.

*Color*.—White like (RHS 155D).

*Petals*.—Five lobed, white like (RHS 155D). Length: 1.5 cm to 3.5 cm. Width: 0.5 mm to 1.5 mm. Shape: oval. Texture (top): smooth. Texture (bottom): smooth.

*Sepals*.—About 5 sepals overlapping in a bell crown. Length: About 0.5 mm. Color: Green like (RHS 140C). Apex description: obtuse. Base description: rounded. Texture: glabrous. Width: 2.5 cm.

*Stamen*.—About 5 to 7 per flower. Filament length: About 1 cm by 0.5 mm in diameter. Filament color is white like (RHS 155D).

*Anthers*.—Broadly oval but slightly irregular in shape, 4 mm long by 1 mm to 2 mm in diameter. Color is greyed-white like (RHS 156C).

*Pollen*.—Yellow like (RHS 10B). Amount: Slight.

*Pedicel*.—Length 1.5 mm; diameter 1 mm; color green like (RHS 142B).

*Peduncle*.—6 cm long by 1.5 mm diameter. Shape: cylindrical. Texture: glabrous. Color: greyed red-like (RHS 180A).

*Fragrance*.—Sweet.

*Flowering season*.—Flowering from May to June.

*Flower longevity on plant*.—Individual flowers last from three to four weeks; flowers not persistent.

*Height*.—1.5 cm.

*Inflorescence*.—Form: pendulous raceme. Arrangement: terminal. Number of flowers per inflorescence: 4 to 8.

Buds:

*Terminal flower buds*.—Length: about 2 to 3 mm. Diameter: about 1 mm. Color: grey-brown like (RHS 199C). Texture: Smooth, glabrous. Shape: oval.

*Lateral flower bud*.—Length: About 2 to 3 mm. Diameter: about 1 mm. Color: brown like (RHS 199C). Texture: Smooth, glabrous. Shape: oval.

Fruit: Shape: Oval. Color: Yellow-green like (RHS 145C). Length: 2.5 to 6 cm. Diameter: 8 cm.

Seed:

*Shape*.—Ovoid with acute apex and base.

*Length*.—8 mm.

*Width*.—5 mm.

*Color*.—Greyed orange like (RHS 166C).

*Number per capsule*.—Typically 1.

Pistil:

*Quantity*.—1.

*Length*.—1.5 cm.

*Texture*.—Smooth.

Ovary:

*Length*.—4 mm.

*Diameter*.—3 mm.

*Shape*.—Rounded.

*Color*.—Greyed purple like (RHS N186C).

Stigma:

*Length*.—5 mm.

*Diameter*.—5 mm.

*Shape*.—Rounded.

*Color*.—White like (RHS N155B).

Style:

*Length*.—16 mm.

*Diameter*.—1 mm.

*Shape*.—Linear.

*Color*.—White like (RHS N155B).

Other characteristics:

Pathogen and pest resistance: Trees of the new *Styrax japonicus* 'SJMTF' variety have no pests or diseases known to the inventor.

Temperature tolerance: Trees of the new *Styrax japonicus* 'SJMTF' variety have been observed to tolerate high temperatures about 95° F. and low temperatures about 10° F. when grown in USDA Hardiness Zone 7b. The new *Styrax japonicus* 'SJMTF' variety is suitable for growing in USDA zones 5 through 8.

What is claimed is:

1. A new and distinct variety of Japanese Snowbell tree named 'SJMTF' as herein shown, illustrated and described.

* * * * *